United States Patent
Nikom

[11] Patent Number: 6,048,314
[45] Date of Patent: Apr. 11, 2000

[54] AUTOMATED MEASUREMENT AND ANALYSIS OF PATIENT ANATOMY BASED ON IMAGE RECOGNITION

[75] Inventor: Jacob Nikom, Needham, Mass.

[73] Assignee: Hewlett-Packard Company, Palo Alto, Calif.

[21] Appl. No.: 09/157,013

[22] Filed: Sep. 18, 1998

[51] Int. Cl.[7] ........................................ A61B 8/00
[52] U.S. Cl. ............................ 600/443; 600/449
[58] Field of Search ................... 600/441, 443, 600/447, 449, 454–456

[56] References Cited

U.S. PATENT DOCUMENTS

| | | | |
|---|---|---|---|
| 4,476,874 | 10/1984 | Taenzer et al. | 600/445 |
| 5,195,521 | 3/1993 | Melton, Jr. et al. | 600/456 X |
| 5,280,787 | 1/1994 | Wilson et al. | 600/456 |
| 5,322,067 | 6/1994 | Prater et al. | 128/916 X |
| 5,465,721 | 11/1995 | Kishimoto et al. | 128/916 X |
| 5,515,857 | 5/1996 | Tsujino et al. | 600/456 |
| 5,538,003 | 7/1996 | Gadonniex et al. | 128/916 |
| 5,555,886 | 9/1996 | Weng et al. | 600/454 |
| 5,622,174 | 4/1997 | Yamazaki | 600/455 X |
| 5,623,930 | 4/1997 | Wright et al. | 600/456 |
| 5,682,896 | 11/1997 | Scheib et al. | 600/456 |
| 5,690,111 | 11/1997 | Tsujino | 600/456 X |

FOREIGN PATENT DOCUMENTS

0775920A1  5/1997  European Pat. Off. .

OTHER PUBLICATIONS

O'Connell, Raymond G., Jr., "The Role of Doppler Ultrasound in Cardiac Diagnosis" Hewlett–Packard Journal, Jun. 1986, pp. 20–25.

Magnin, P.A., "Doppler Effect: History and Theory"id. at pp. 26–31.

Halberg, L.I. et al Extraction of Blood Flow Information Using Doppler–Shifted Ultrasound, id. at pp. 35–40.

Hunt, B. F. et al, "Digital Processing Chain for a Doppler Ultrasound Subsystem", id. at pp. 45–48.

*Primary Examiner*—Francis J. Jaworski

[57] ABSTRACT

Methods and apparatus are provided for measurement and analysis of patient anatomy with an ultrasound imaging system which generates an ultrasound image of a region of a patient and provides coordinates of walls of vessels in the image. In response to placement of a cursor within the vessel in the ultrasound image, one or more parameters of the vessel in the vicinity of the cursor are determined automatically from the wall coordinates. The determined parameter values are recorded. The vessel parameters may include vessel diameter, vessel center coordinates and/or vessel wall directions. The vessel may be automatically mapped by moving the cursor to multiple positions along the vessel and determining the parameters of interest at each cursor position. The smallest vessel diameter may be determined and highlighted in the ultrasound image.

24 Claims, 9 Drawing Sheets

AUTOMATED MEASUREMENT AND ANALYSIS OF PATIENT ANATOMY BASED ON IMAGE RECOGNITION

CROSS-REFERENCE TO RELATED APPLICATION

This application is related to commonly assigned U.S. patent application Ser. No. 09/157,010, filed on even date herewith in the name of Alfred Langguth, and entitled "Method And Apparatus For Assisting A User In Positioning An Ultrasound Transducer".

FIELD OF THE INVENTION

This invention relates to the field of medical ultrasound imaging and, more particularly, to methods and apparatus for measurement and analysis of patient anatomy by analysis of ultrasound images.

BACKGROUND OF THE INVENTION

The use of ultrasonic imaging for medical diagnostic purposes is well known. In particular, ultrasound has been used for many years to aid in the diagnosis of certain cardiac diseases. In addition, cardiac Doppler ultrasound technology has become recognized as an important tool in the evaluation of cardiac blood flow rates. In Doppler ultrasound imaging, a reflection from a stationary object provides a signal at zero frequency (that is, at the intermediate frequency). The Doppler frequency shift in the echo signal returned from a moving target varies monotonically with the instantaneous velocity of the target. A review of cardiac Doppler measurement technology is contained in R. G. O'Connell, Jr., "The Role of Doppler Ultrasound in Cardiac Diagnosis," *Hewlett-Packard Journal*, June 1986 at 20–25; in P. A. Magnin, "Doppler Effect: History and Theory," id. at 26–31; in L. I. Halberg et al, "Extraction of Blood Flow Information Using Doppler-Shifted Ultrasound," id. at 35–40; and in B. F. Hunt et al, "Digital Processing Chain for A Doppler Ultrasound Subsystem," id. at 45–48.

A typical prior art medical ultrasound imaging system employs a phased array transducer, a scanner unit and a signal processing and display unit. The scanner unit provides analog signal conditioning, beamforming and signal translation from the ultrasound range to a more convenient intermediate frequency (I.F.) range. The processing and display unit then converts the analog I.F. signals to digital form and processes the digital samples in order to facilitate extraction and display of desired information contained in the transducer output. The display and processing unit may provide both black and white (monochrome) and color imaging. The monochrome mode typically is used to show anatomic detail, with blood flow shown in the color mode. In a typical system, a two-dimensional monochrome image may show a sector-shaped scan region of a patient, displayed at a rate of approximately 30 frames per second. A color mode image may be overlaid on a portion (up to 100%) of the scanned sector, displacing the monochrome image. At each picture element on the display, either the monochrome signal or the color signal is displayed; alternatively, the two signals may be combined in some fashion.

The color image is typically a color-coded blood flow map, where the color coding indicates localized velocity and turbulence of blood flow. In an exemplary commercial system, velocity is shown in shades of red and blue, red indicating flow toward the transducer and blue indicating flow away from the transducer, or vice versa. Sometimes another color may be mixed in over a portion of the scale to focus attention on flows within selected ranges. The intensity and/or shading of the color represents the speed of the flow toward or away from the transducer. Shades of green are sometimes added to indicate turbulence.

While the ultrasound image provides a qualitative representation of the region of interest, it is frequently desirable to obtain quantitative measurements of vessel parameters, such as blood velocity, vessel diameter and vessel wall directions. In order to determine blood velocity, the angle between the ultrasound beam direction and the direction of the blood vessel must be determined. A method for adjustment of Doppler angle in ultrasound images is disclosed in European Patent Application No. 0,755,920 published May 28, 1997. This published application describes a vessel analysis algorithm for calculating the direction of the vessel and coordinates of the vessel walls in the vicinity of the cursor when the cursor is positioned inside of a vessel in the ultrasound image.

Known techniques for quantitatively determining parameters such as blood velocity and vessel diameter from ultrasound images have been relatively difficult to use and have been time-consuming. In addition, such techniques have required relatively skilled operators and do not produce consistent results. Accordingly, it is desirable to provide methods and apparatus for automated measurement and analysis of patient anatomy from ultrasound images which overcome the drawbacks of prior art techniques. In particular, it is desirable to reduce the amount of training necessary to obtain such measurements from ultrasound images, to reduce or eliminate the variability of results related to differences between ultrasound operators, to diminish the influence of screen resolution on measurement results, to reduce overall ultrasound measurement time and to decrease operator stress and workload.

SUMMARY OF THE INVENTION

According to a first aspect of the invention, a method is provided for measurement and analysis of patient anatomy with an ultrasound imaging system which generates an ultrasound image of a region of a patient and provides coordinates of walls of a vessel in the image. In response to placement of a cursor within the vessel in the ultrasound image, one or more parameters of the vessel in the vicinity of the cursor are determined from the wall coordinates. The determined parameter values are recorded. The vessel parameters may include vessel diameter, vessel center coordinates and/or vessel wall directions.

A center of gravity of the pixels defining the upper vessel wall and a center of gravity of the pixels defining the lower vessel wall may be determined from the wall coordinates. The vessel diameter and the vessel center coordinates may be determined from the centers of gravities of the pixels defining the upper and lower vessel walls.

According to a further feature of the invention, the cursor may automatically be moved to the vessel center coordinates in the ultrasound image and may be rotated into alignment with the vessel wall directions. The cursor is then moved along the vessel in the cursor direction to a new position and the process of determining one or more vessel parameters is performed at the new cursor position. By repeating this process, the vessel is automatically mapped.

As the cursor is moved to the new cursor position, contact between the cursor and the vessel wall in the ultrasound image may be sensed. The cursor is moved by incremental moves, and a pixel value of the image is compared with a threshold value representative of the vessel wall after each incremental move. Additionally, as the cursor is moved to the new cursor position, the end of the vessel in the ultrasound image may be sensed by determining that the upper and lower vessel wall directions exceed a predetermined angle.

According to another feature of the invention, coordinates of the smallest diameter of the vessel may be identified. The smallest diameter may be highlighted in the ultrasound image.

According to yet another feature of the invention, actual cursor movement may be constrained within the vessel in response to requested cursor movement by a user.

According to a further aspect of the invention, apparatus for measurement and analysis of patient anatomy is provided. The apparatus comprises an ultrasound imaging system for generating an ultrasound image of a region of a patient and for providing coordinates of walls of a vessel in the image. The apparatus further comprises means responsive to placement of the cursor within the vessel in the ultrasound image for determining from the wall coordinates one or more parameters of the vessel in the vicinity of the cursor and means for recording the determined parameter values.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
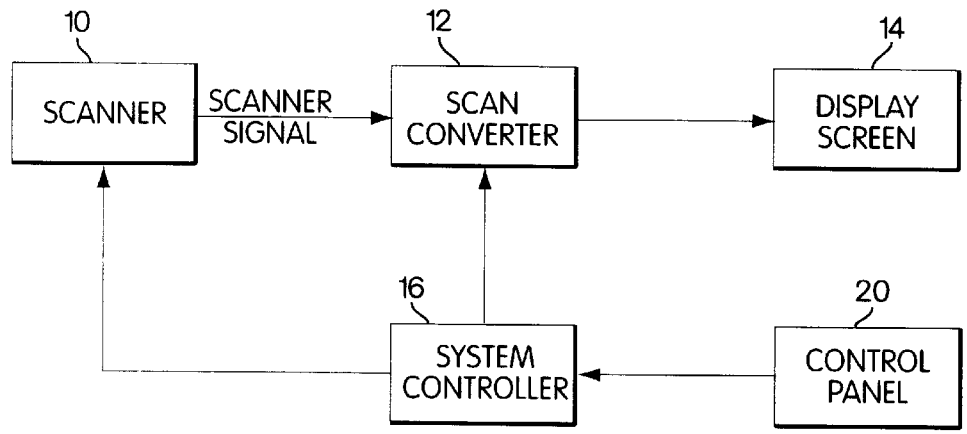
FIG. 1 is a simplified block diagram of an example of an ultrasound imaging system suitable for incorporation of the present invention.

A simplified block diagram of an example of an ultrasound imaging system suitable for incorporation of the present invention is shown in FIG. 1. A scanner 10 performs ultrasound scanning of a target region of a patient's body. The scanner 10 includes an ultrasound transducer for transmitting and receiving ultrasound energy. The transducer transmits ultrasound energy into the target region and receives reflected ultrasound energy from various structures, tissues and organs within the patient's body.

The transducer may include an array of transducer elements. As known in the prior art, by appropriately delaying the pulses applied to each transducer element, a focused ultrasound beam is transmitted along a desired scan line. Reflected ultrasound energy from a given point within the patient's body is received by the transducer elements at different times. The transducer elements convert the received ultrasound energy to electrical signals which are supplied to a receive beamformer. The delayed signals from each transducer element are summed by the beamformer to provide a scanner signal that represents the reflected energy level along a given scan line. The process is repeated for multiple scan lines to provide signals for generating an image of the target region of the patient's body. The scan pattern may be a sector scan, wherein scan lines originate at the center of the ultrasound transducer and are directed at different angles. A linear, curvilinear or any other scan pattern can also be utilized.

The scanner signal is supplied to a scan converter 12, which converts the scanner signal generated by scanner 10 to a conventional raster display signal. The output of scan converter 12 is supplied to a video display screen 14, which displays an image of the target region of the patient's body. A system controller 16 provides overall control of the system. The system controller 16 performs timing and control functions and may include a microprocessor and associated memory. A control panel 20 permits user control of the system. The control panel 20 may, for example, include a conventional alphanumeric keyboard, dedicated function keys, a trackball, one or more touch panels and various adjustment controls. The trackball permits control of the position of the cursor on the display screen 14 in operating modes where a cursor is utilized. An example of an ultrasound imaging system suitable for incorporation of the present invention is the Sonos GP 8500, manufactured and sold by Hewlett-Packard Company.

According to a feature of the present invention, patient anatomy is measured and analyzed by automated analysis of ultrasound images. The invention is particularly useful in connection with measurement and analysis of parameters related to blood vessels, including but not limited to blood velocity, vessel diameter, vessel center coordinates, and vessel wall directions. These parameters may be determined automatically at a series of points along the vessel, thereby mapping the vessel. The determined parameters may be recorded, such as in a computer memory, for recordkeeping purposes and/or for analysis. In addition, the determined parameters may be displayed on a display screen, may be printed, may be transmitted to another location or may be processed and/or recorded in any desired manner.

Figure 2:
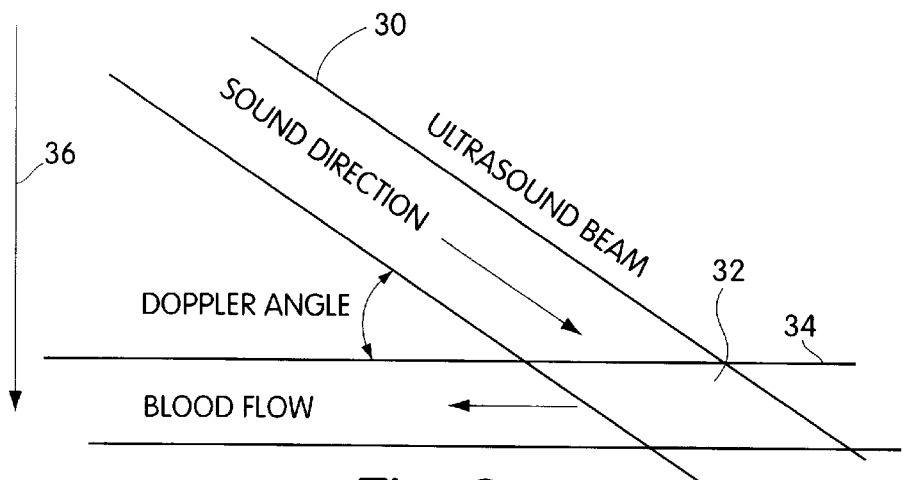
FIG. 2 illustrates the parameters associated with Doppler measurement of blood velocity.
Figure 3:
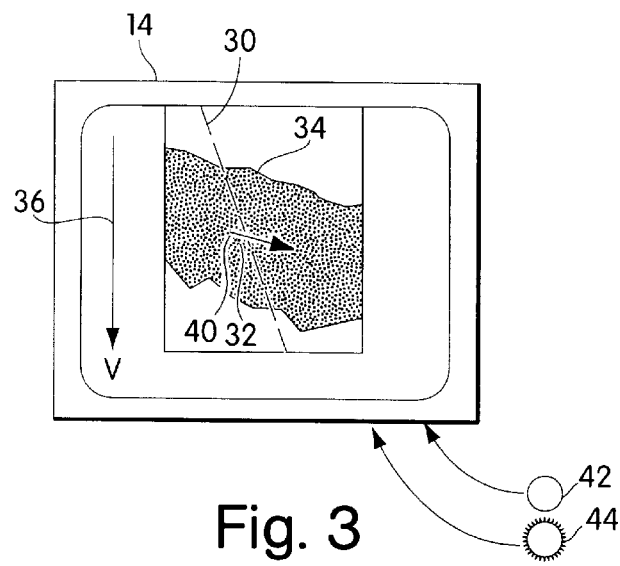
FIG. 3 is a schematic representation of a Doppler ultrasound image display.

Parameters associated with determining blood velocity using Doppler imaging techniques are shown in the schematic diagram of FIG. 2. A schematic diagram of a Doppler ultrasound image is shown in FIG. 3. An ultrasound beam 30 is directed to a region of interest 32 in a blood vessel 34. An image of blood vessel 34 is presented on display screen 14, which has a vertical direction 36. As known in the art, blood velocity, V, in region of interest 32 is given by $$V = k * f_D / f_O * \cos\theta \tag{1}$$

where k is a dimensional coefficient, $f_O$ is the transducer output frequency and $f_D$ is the Doppler frequency shift between the transducer output frequency and the frequency of the ultrasound echo. In order to calculate blood velocity, it is necessary to know the Doppler angle $\theta$ between ultrasound beam 30 and blood vessel 34 in the region of interest 32.

In prior art blood velocity measurements, the user positions a cursor 40 in the region of interest 32 using a trackball 42 and rotates the cursor 40 into alignment with the blood vessel direction using a rotary control 44. The cursor direction, which is aligned with the blood vessel, is then used to determine the Doppler angle $\theta$. The Doppler angle is used to calculate blood velocity in accordance with equation (1). The transducer output frequency $f_O$ is known, and the Doppler frequency shift $f_D$ is determined from the return echo using known techniques.

The aforementioned European Patent Application No. EP 0 755 920 A1 describes a vessel analysis algorithm having the ability to calculate vessel direction and the coordinates of the vessel walls in the vicinity of the cursor when the cursor is placed inside the vessel in the ultrasound image. The vessel analysis algorithm 100 is described on page 2 of European Application No. EP 0 755 920 A1. The user places the cursor inside the vessel using the trackball and starts the vessel analysis algorithm. The algorithm calculates the vessel direction and sends it to the graphical subsystem associated with the display screen, which rotates the cursor on the display screen.

Figure 4:
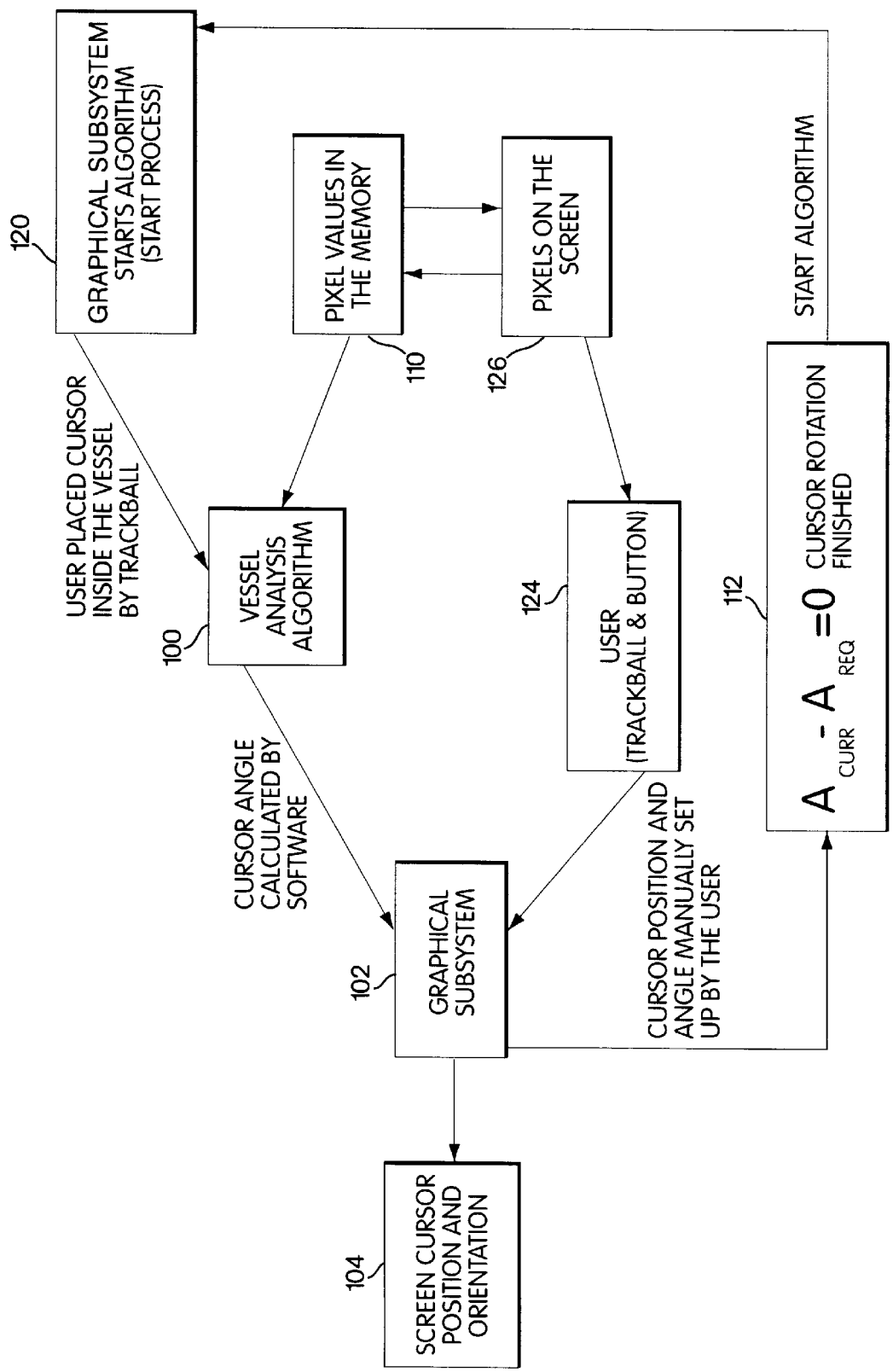
FIG. 4 is a flow diagram that illustrates cursor control in accordance with the invention.

In accordance with a feature of the invention, cursor positioning and rotation are automated, as shown in the flow diagram of FIG. 4. The user places the cursor inside the vessel using the trackball 42 and starts the vessel analysis algorithm 100. The vessel analysis algorithm supplies a cursor angle to graphical subsystem 102 of the ultrasound imaging system. The graphical subsystem 102 controls screen cursor position and orientation 104. As shown in FIG. 4 the vessel analysis algorithm 100 uses pixel values 110 stored in the memory of the ultrasound imaging system. When the cursor has been rotated to the desired angle as determined in step 112, a new iteration of the vessel analysis algorithm may be started in step 120. Each iteration of the vessel analysis algorithm may be based on the same cursor position or a different cursor position. As shown in FIG. 4, the user may manually position the cursor in step 124 based on screen pixels 126. Subsequent cursor positions may be determined automatically without user intervention, as described below.

Figure 5:
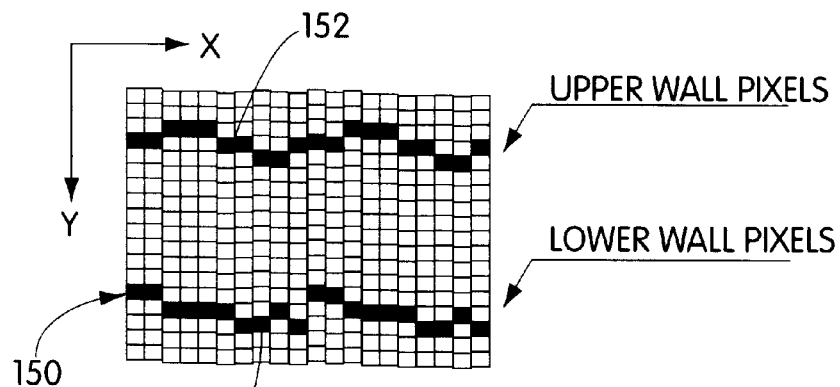
FIG. 5 is a partial representation of an ultrasound image of a blood vessel, illustrating pixels used to calculate vessel wall center.

Additional features of the invention are described with reference to FIGS. 5–8. An example of a portion of an ultrasound image is shown in FIG. 5. A blood vessel 150 includes an upper vessel wall 152 and a lower vessel wall 154. Each vessel wall is represented in the image by a plurality of pixels having a positions that correspond to the position of the vessel wall. Typically, the vessel wall has a thickness of several pixels. Each pixel has pixel x, y coordinates and a pixel value that defines pixel intensity in the ultrasound image. Normally, the pixel values of the vessel walls differ from the pixel values representative of blood in the vessel interior.

The coordinates of the vessel wall center of gravity $X_{w/c}$ and $Y_{w/c}$ may be calculated as follows:

$$Y_{wc} = \frac{\sum_{i=1}^{i=N} y_i}{N} \tag{2}$$

Where $x_i$ and $y_i$ represent coordinates of the I-th pixel in the vessel wall and N is the number of vessel wall pixels processed by the vessel analysis algorithm.

$$X_{wc} = \frac{\sum_{i=1}^{i=N} x_i}{N} \tag{3}$$

Figure 6:
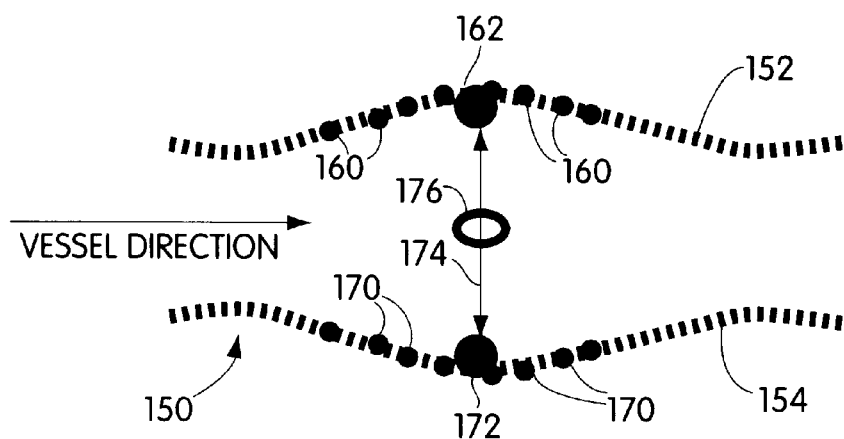
FIG. 6 is a schematic representation of an image of a blood vessel, illustrating parameters associated with calculation of vessel diameter and vessel center.

The vessel diameter and the vessel center in the vicinity of the cursor are calculated from the vessel wall centers of gravity as shown in FIG. 6. Upper vessel wall pixels 160 are used to calculate an upper wall center of gravity 162, and lower vessel wall pixels 170 are used to calculate a lower wall center of gravity 172, each being calculated in accordance with equations (2) and (3) above. A vessel diameter, d, may be calculated as follows:

$$d = \sqrt{(x_{up} - x_{lo})^2 + (y_{up} - y_{lo})^2} \tag{4}$$

Where $x_{up}$ and $y_{up}$ are coordinates of the upper wall center of gravity and $x_{lo}$ and $y_{lo}$ are coordinates of the lower wall center of gravity. In addition, coordinates of the vessel center, $x_{vc}$ and $y_{vc}$, may be calculated as follows:

$$x_{vc} = (x_{up} + x_{lo})/2 \tag{5}$$

$$y_{vc} = (y_{up} + y_{lo})/2 \tag{6}$$

Figure 7:
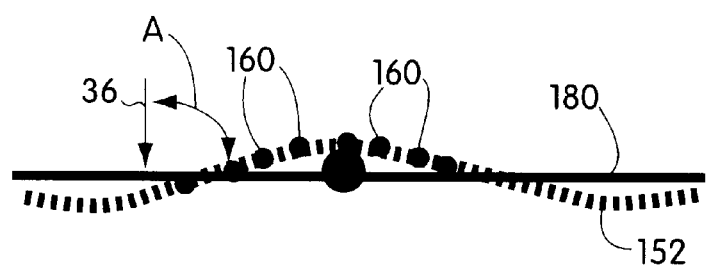
FIG. 7 is a schematic representation of a vessel wall, illustrating parameters associated with calculation of vessel wall direction.

The direction of each vessel wall may then be calculated. As shown in FIG. 7, each vessel wall direction is calculated from a group of pixels in the vicinity of the cursor. In particular, upper vessel wall pixels 160 are used to determine an angle A between an upper wall direction 180 of vessel wall 152 and vertical direction 36 of the display screen as follows:

$$tg\, A = \frac{N \sum_{i=1}^{i=N} x_i y_i - \sum_{i=1}^{i=N} x_i \sum_{i=1}^{i=N} y_i}{N \sum_{i=1}^{i=N} x_i x_i - \sum_{i=1}^{i=N} x_i \sum_{i=1}^{i=N} x_i} \tag{7}$$

Where tg A represents the tangent of angle A and $x_i$ and $y_i$ are the coordinates of the I-th pixel in the vessel wall. The directions of the upper and lower vessel walls may be determined in the same manner.

Figure 8:
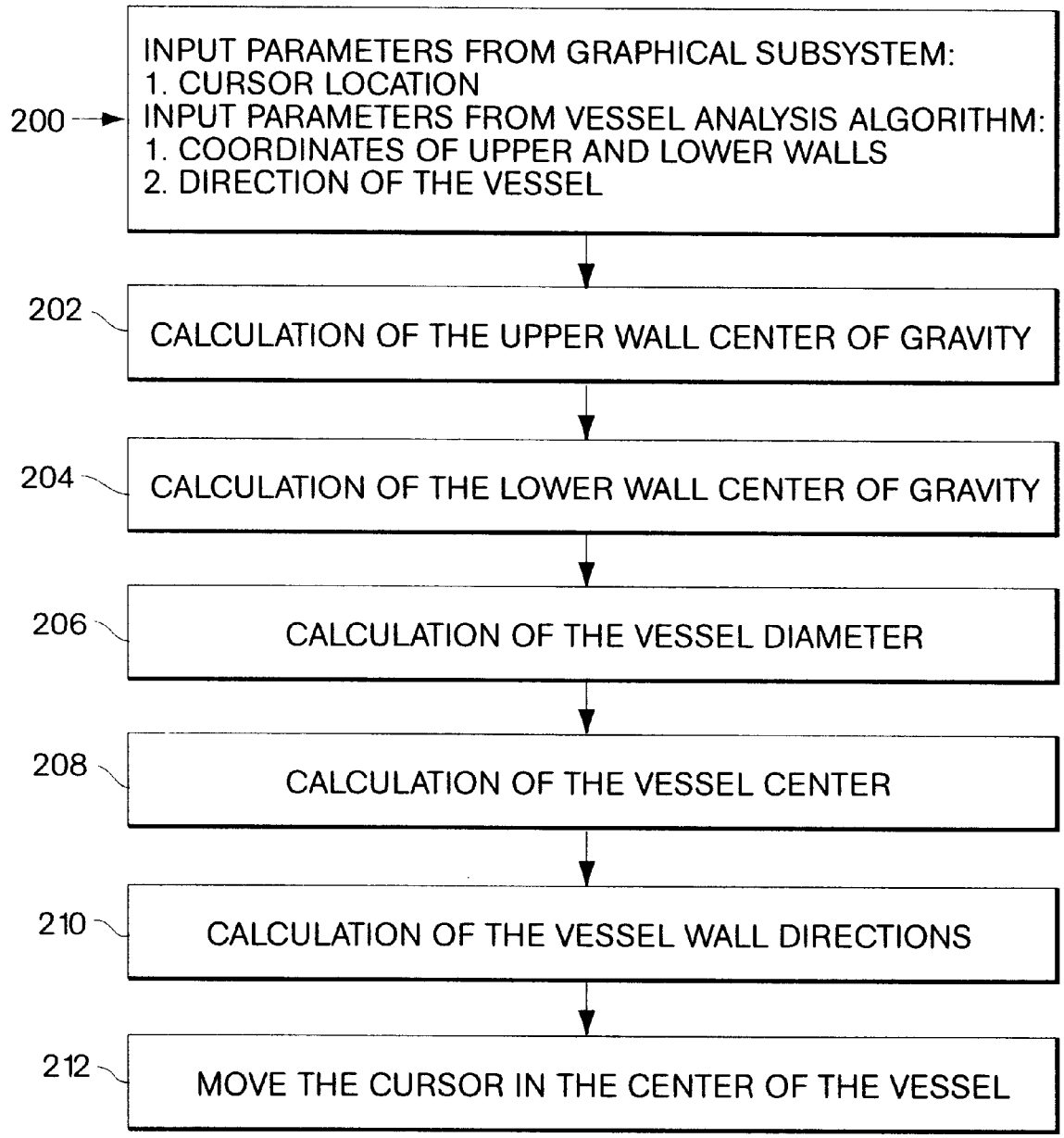
FIG. 8 is a flow chart of a process for determining vessel center, vessel diameter and vessel wall direction.

The above operations are summarized in the flow chart of FIG. 8. The process receives the coordinates of the cursor from the graphical subsystem and receives the coordinates of the upper and lower wall pixels and the direction of the vessel from the vessel analysis algorithm in step 200. Then the upper wall center of gravity is calculated in step 202, and the lower wall center of gravity is calculated in step 204 as described above in connection with FIGS. 5 and 6 and equations (2) and (3). The vessel diameter is calculated in step 206 as described above in connection with FIG. 6 and equation (4). The vessel center is calculated in step 208 as described above in connection with FIG. 6 and equations (5) and (6). The vessel wall directions are calculated in step 210 as described above in connection with FIG. 7 and equation (7). When the calculations of steps 202–210 are completed, the graphical subsystem in step 212 places the cursor in the center of the vessel, indicates the vessel diameter to the user and rotates the cursor into alignment with the vessel direction as indicated by the upper and lower vessel wall directions. When the operations of FIG. 8 have been completed, another iteration may be initiated, as indicated in FIG. 4 and described above.

According to a further feature of the invention, automatic tracking of the vessel may be performed. Following the operations shown in FIG. 8 and described above, the following parameters are known (1) the cursor location at the vessel center; (2) the vessel diameter at the cursor location; (3) the vessel direction at the cursor location; and (4) the vessel wall threshold. The vessel wall threshold is used to determine contact between the cursor and the vessel wall by identifying pixels which correspond to the vessel wall. In particular, pixels within the blood vessel which represent blood have pixel values in a first range, and pixels that represent the vessel wall have pixel values in a second range. The vessel wall threshold is set between the first and second ranges of pixel values. Thus, when pixels have values that exceed the wall threshold, they are classified as representing the vessel wall.

Figure 9:
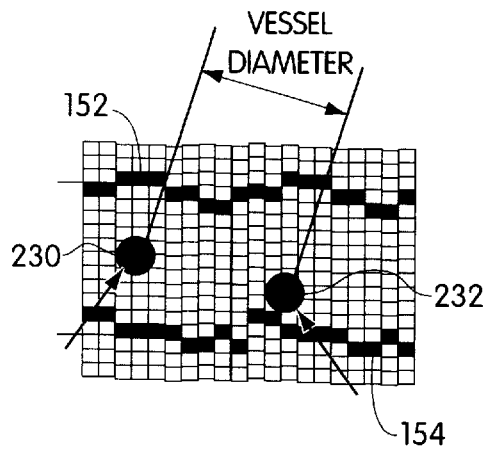
FIG. 9 is a partial representation of an ultrasound image of a blood vessel, illustrating cursor movement in the vessel direction.

Based on this knowledge, the process may then move the cursor to a new location as shown in FIG. 9. In particular, the cursor is moved from a current position 230 to a new position 232. The cursor is moved in the vessel direction from the current cursor position 230. The pixel values along the direction of cursor movement are read and are compared with the wall threshold. If the pixel values do not exceed the wall threshold, the cursor may be moved by a distance equal to the vessel diameter as indicated in FIG. 9. When the pixel values do not exceed the wall threshold as the cursor is moved, it is assumed that the cursor remains within the vessel walls. At new cursor position 232, the operations shown in FIG. 8 and described above are repeated, thus providing values of vessel diameter, vessel center and vessel wall directions. This process may be repeated at multiple cursor positions along the vessel, so as to track the entire vessel and provide vessel parameter values at each cursor position.

Figure 10:
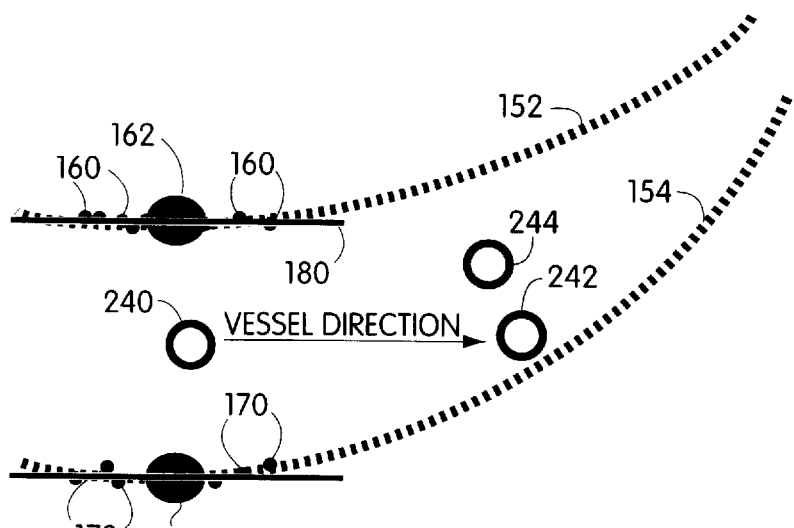
FIG. 10 is a schematic representation of an ultrasound image of a blood vessel, illustrating cursor movement which results in contact with the vessel wall, followed by cursor repositioning.

A special case of cursor movement is illustrated in FIG. 10. Movement of the cursor from current cursor position to 240 to new cursor position 242 results in the cursor contacting lower vessel wall 154 before it has moved by the vessel diameter. As indicated above, contact with the vessel wall is determined by comparison of pixel values along the direction of cursor movement with the wall threshold. The operations shown in FIG. 8 and described above are performed at new cursor position 242 where the cursor contacts the vessel wall. The cursor is then moved to the vessel center at position 244. The cursor may then be moved from position 244 to the next cursor position, by a distance equal to the vessel diameter in the vessel direction.

Figure 11:
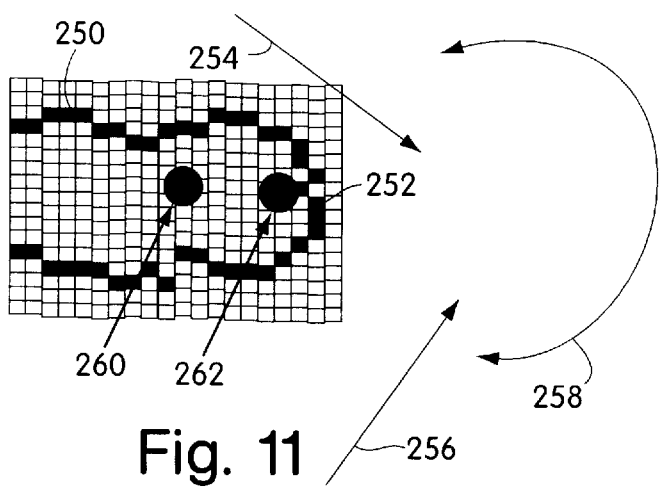
FIG. 11 is a partial representation of an ultrasound image of a blood vessel, illustrating cursor movement along the vessel direction to the end of the vessel in the ultrasound image.

Another special case of cursor movement is illustrated in FIG. 11. The image of a blood vessel may end within the ultrasound image. As shown in FIG. 11, vessel 250 has an end 252. Although the patient's blood vessel does not actually end, the image of the vessel may end due to the fact that the blood vessel bends out of the image plane. The vessel end may be determined from the upper vessel wall direction 254 and the lower vessel wall direction 256, which are calculated at each cursor position, such as cursor positions 266 and 262. Except near the vessel end, the upper and lower wall directions 254 and 256 are more or less parallel. Near the end of the vessel, the upper and lower wall directions 254 and 256 converge as shown in FIG. 11. Thus, the vessel end may be identified by comparing the upper and lower wall directions 254 and 256 at cursor position 262 where the cursor contacts the vessel wall. Where an angle 258 between the upper and lower wall directions 254 and 256 exceeds a given value, such as 120°, the vessel end is indicated. When the vessel end is reached, the tracking procedure is complete.

Figure 12:
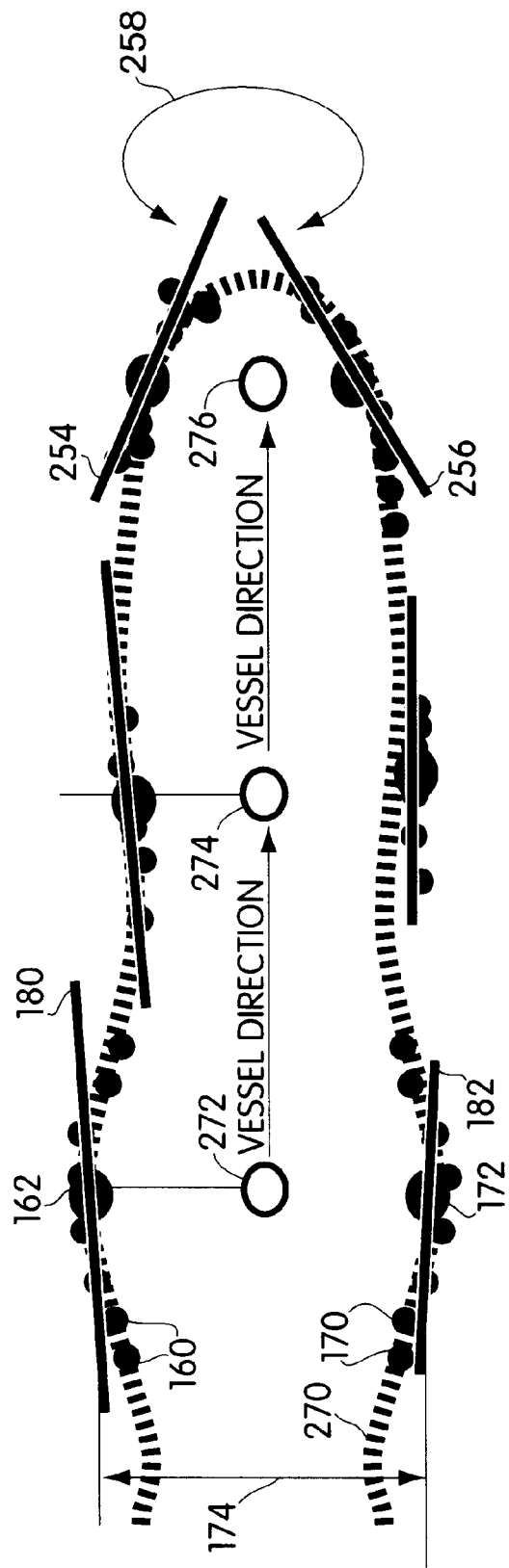
FIG. 12 is a schematic representation of an ultrasound image of a blood vessel, illustrating automatic mapping of vessel parameters.

Vessel tracking is illustrated schematically in FIG. 12. A vessel 270 is mapped in an ultrasound image. The cursor is successively moved to positions 272, 274 and 276. In each case, the cursor may be moved in the vessel direction by the vessel diameter, unless the cursor contacts the vessel wall or the vessel end as described above. It will be understood that the specified movement distance may be more or less than the vessel diameter, depending on the desired mapping accuracy and speed. At each cursor location, the upper and lower wall centers of gravity 162 and 172, the vessel diameter 174, the coordinates of vessel center 272 and the vessel wall directions 180 and 182 are determined. The determined parameters are recorded, such as by storing them in a memory, printing them and/or displaying them on a display screen. In a typical vessel tracking operation, multiple cursor positions are required, depending on the length of the vessel in the ultrasound image.

Figure 13:
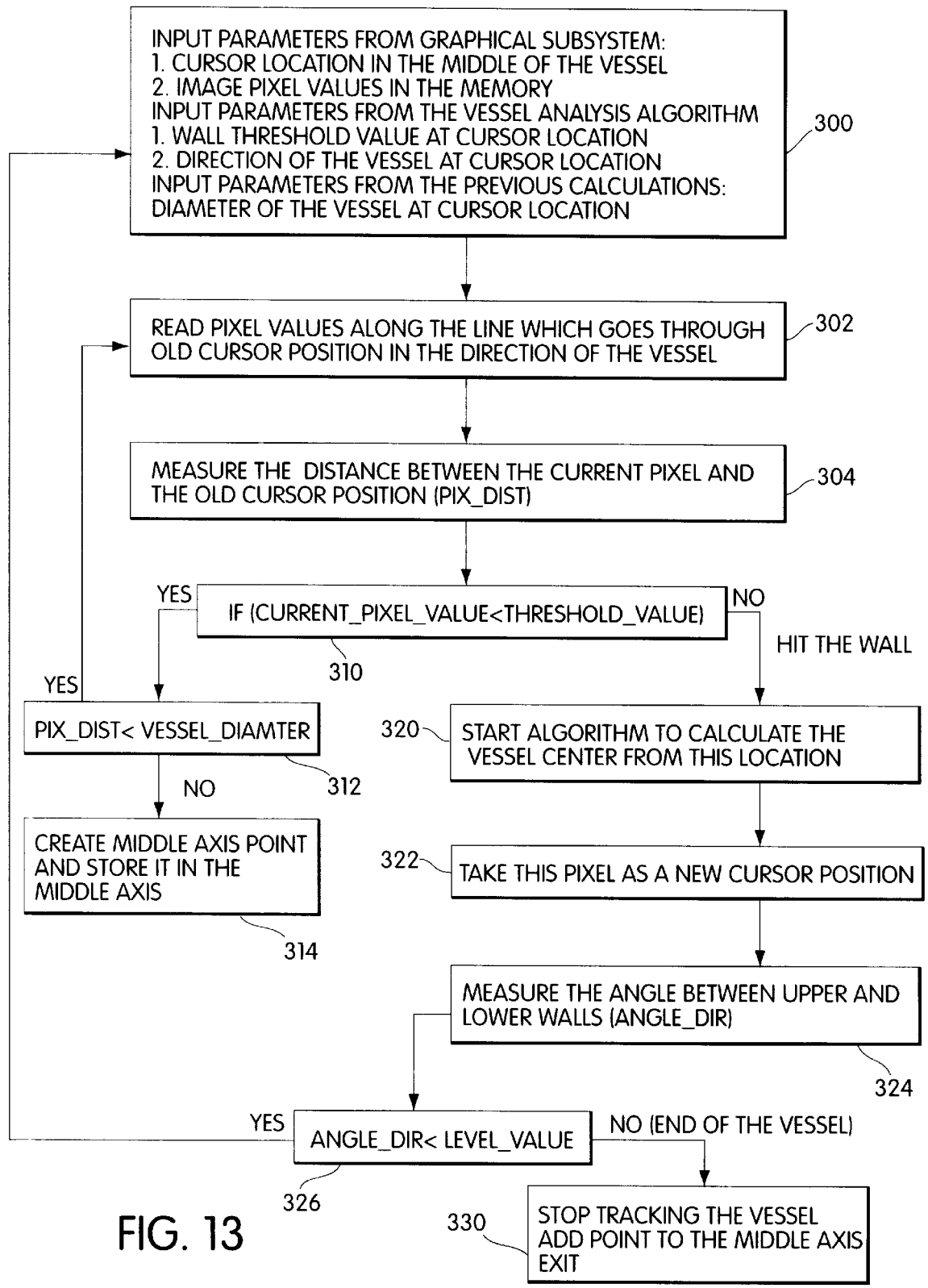
FIG. 13 is a flow chart of a process for vessel tracking in accordance with the invention.

An example of the vessel tracking process is summarized in the flow chart of FIG. 13. In step 300, parameters required for vessel tracking are input from the graphical subsystem, from the vessel analysis algorithm and from previous calculations. Parameters input from the graphical subsystem include cursor location at the vessel center and image pixel values in the vicinity of the cursor. Parameters input from the vessel analysis algorithm include wall threshold at the cursor location and direction of the vessel at the cursor location. The diameter of the vessel at the cursor location is input from previous calculations. In step 302, pixel values along a line through the current cursor position in the vessel direction are read. The distance between the current pixel and the old cursor position is determined in step 304. A determination is made in step 310 as to whether the current pixel value is less than the wall threshold value. When the current pixel value is less than the wall threshold value, a determination is made in step 312 as to whether the distance between the current pixel and the old cursor position is less than the vessel diameter. When the pixel distance is not less than the vessel diameter, a middle axis point is created and stored in step 314. The operations shown in FIG. 8 and described above are performed for the middle axis point. When the pixel distance is determined in step 312 to be less than the vessel diameter, the process returns to step 302 to continue reading pixel values along the direction of movement.

When a determination is made in step 310 that the current pixel value is not less than the wall threshold value, indicating contact with the vessel wall, the vessel center and other parameters corresponding to this cursor position are calculated in step 320. The calculated vessel center is designated in step 322 as the new cursor position. In step 324, the angle between the upper and lower wall directions is determined. In step 326 the angle between the upper and lower vessel wall directions is compared with a predetermined value. When the angle between vessel wall directions is less than the predetermined value, the process returns to step 300. When the angle between vessel wall directions is not less than the predetermined value, indicating the end of the vessel, vessel tracking is terminated in step 330, and the cursor position is added to the data defining the middle axis of the vessel.

Figure 14:
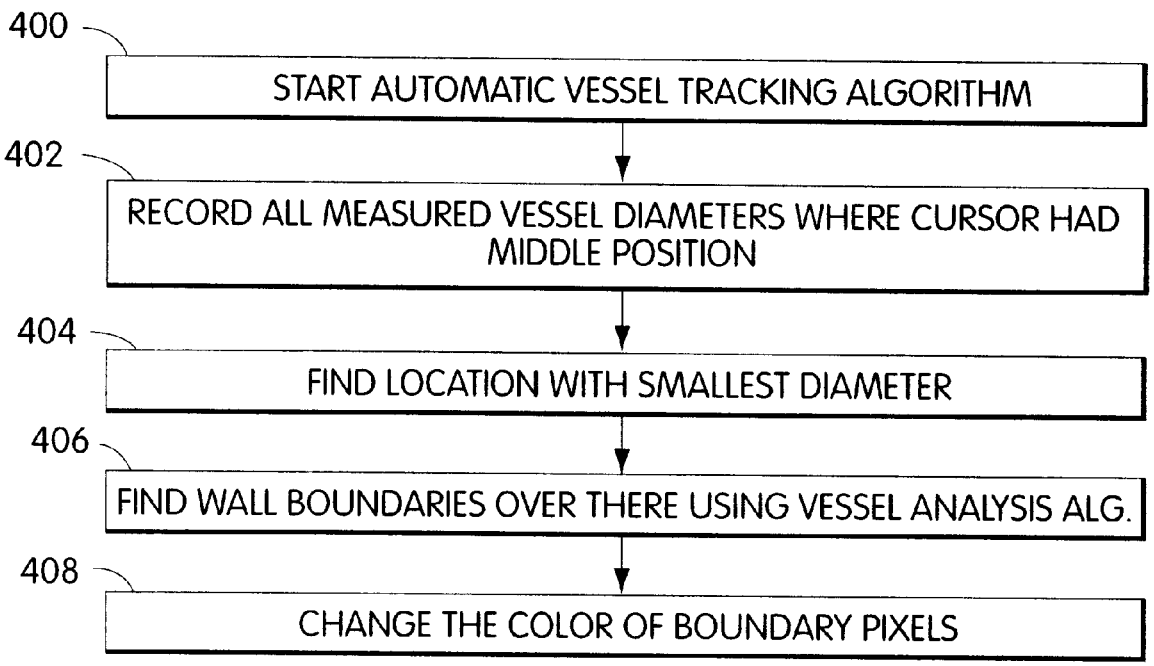
FIG. 14 is a flow chart of a process for determining the vessel location with the smallest diameter and highlighting the smallest diameter in the ultrasound image.

According to a further feature of the invention, the smallest diameter of the blood vessel may be found and highlighted in the ultrasound image. A narrowing of the vessel is of particular interest to the clinician and is advantageously highlighted. A flow chart of an example of a process for locating and highlighting the smallest vessel diameter is shown in FIG. 14. The automatic vessel tracking algorithm is started in step 400. The automatic vessel tracking routine is executed, as described above in connection with FIGS. 8 and 13. In step 402 all vessel diameters are recorded. In step 404, the vessel coordinates having the smallest vessel diameter are found. The wall boundaries at the location with the smallest diameter are found using the vessel analysis algorithm in step 406. The pixels of the vessel wall in the vicinity of the smallest vessel diameter are changed in color in step 408. It will be understood that other highlighting techniques may be utilized.

Figure 15:
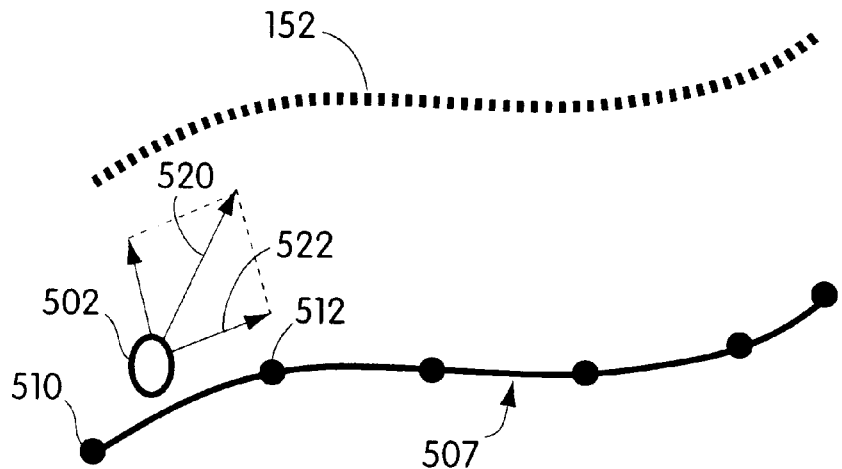
FIG. 15 is a schematic representation of an ultrasound image of a blood vessel, illustrating the parameters associated with constraining cursor movement to the middle axis of the vessel.
Figure 15:
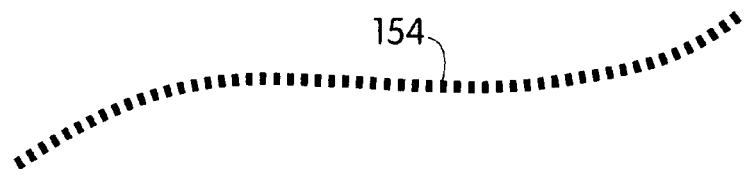
Figure 16:
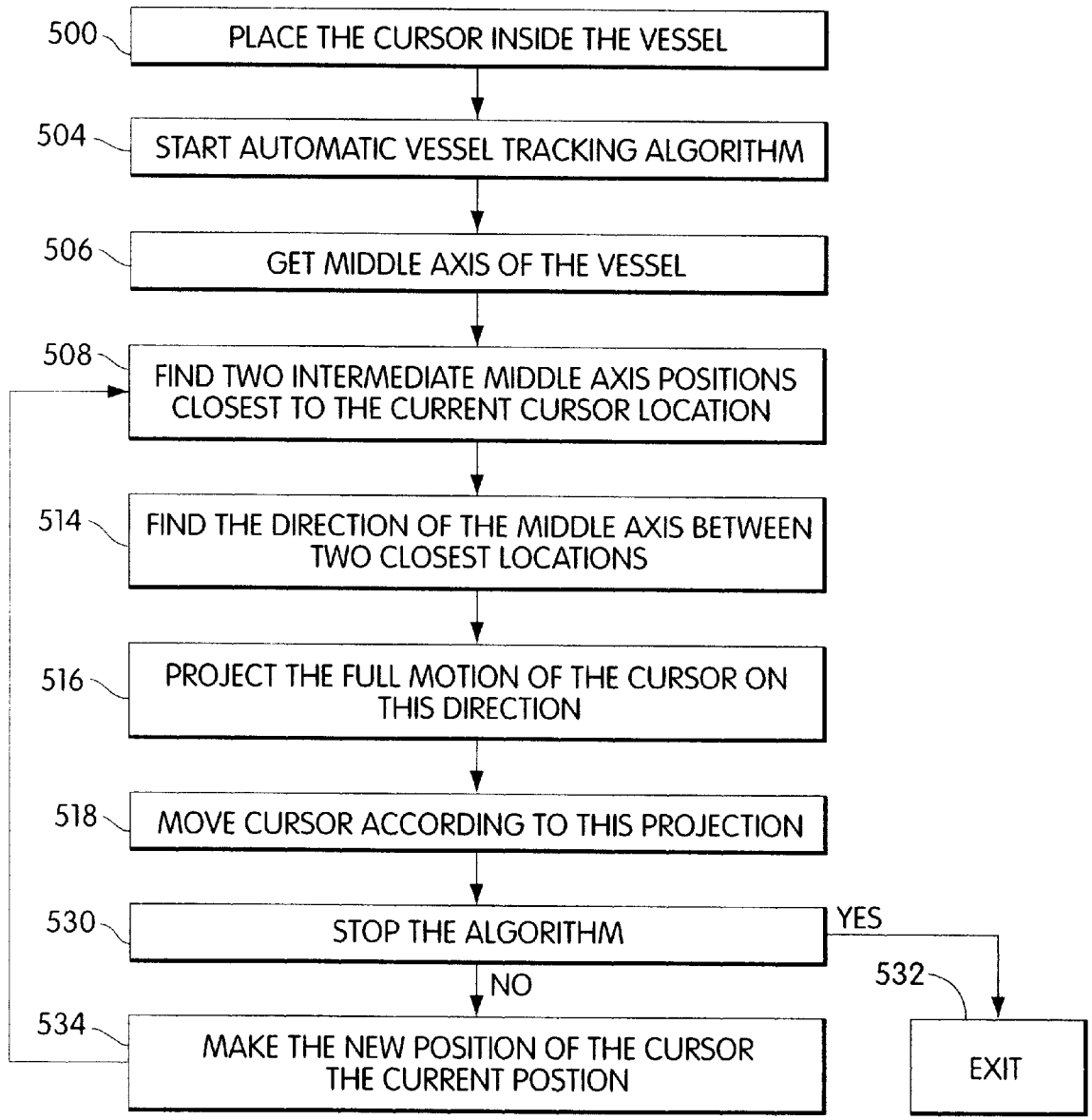
FIG. 16 is a flow chart of a process for constraining cursor movement to the vessel middle axis in accordance with the invention.

A further feature of the invention is described with reference to FIGS. 15 and 16. This feature is useful where the user tries to track the vessel by manually moving the cursor along the middle axis of the vessel. The user may rotate the trackball with one hand while holding the ultrasound transducer on the patient with the other hand and may not be able to precisely observe whether the cursor is located inside the vessel. The following process maintains the cursor inside the vessel automatically.

First, user places the cursor at any point inside the vessel in step 500. An initial cursor position 502 is indicated in FIG. 15. The automatic vessel tracking routine is started in step 504, and the middle axis of the vessel is determined in step 506. The process determines a middle axis 507 of the vessel along which every point is equidistant from both vessel walls. In step 508, two intermediate middle axis positions, such as positions 510 and 512 in FIG. 15, which are closest to the current cursor position 502, are determined. The direction of the middle axis 507 between the two closest middle axis positions 510 and 512 is determined in step 514. Cursor motion is projected on this direction in step 516. The cursor is moved by an amount equal to the projection of the full cursor motion on the middle axis direction in step 518. Thus, with reference to FIG. 15, cursor movement by the operator in direction 520 produces an actual cursor movement in a direction and by a distance indicated by arrow 522. Movement 522 is parallel to the line between middle axis points 510 and 512 by a distance equal to the projection of movement 520 in the middle axis direction. If operator movement of the cursor has stopped as determined in step 530, the process is terminated in step 532. Otherwise, the new cursor position is made the current cursor position in step 534. The process then returns to step 508 to continue tracking the middle axis of the vessel.

The process analyzes cursor movement by the operator. The cursor movement is decomposed into two components, one parallel to the vessel middle axis and the other perpendicular to the vessel middle axis, as shown in FIG. 15. The actual movement of the cursor is determined only by the parallel component 522. Thus, the cursor stays close to the vessel middle axis.

Having thus described certain embodiments of the present invention, various alterations, modifications, and improvements will readily occur to those skilled in the art. Such alterations, modifications, and improvements are intended to be within the spirit and scope of the invention. Accordingly, the foregoing description is by way of example only, and not intended to be limiting. The invention is limited only as defined in the following claims and the equivalents thereof.

What is claimed is:

1. A method for measurement and analysis of patient anatomy with an ultrasound imaging system which generates an ultrasound image of a region of a patient and provides coordinates of walls of a vessel in the image, said ultrasound imaging system executing the steps of:
   a) in response to placement of a cursor within the vessel in the ultrasound image, automatically determining from the wall coordinates values of one or more parameters of the vessel in the vicinity of the cursor;
   b) recording the determined parameter values; and
   c) automatically moving the cursor to a plurality of positions along the vessel and repeating steps a) and b) at each of said plurality of positions, thereby automatically tracking the vessel.

2. A method as defined in claim 1 wherein the step of determining values of one or more parameters comprises determining a diameter of the vessel in the vicinity of the cursor.

3. A method as defined in claim 1 wherein the step of determining values of one or more parameters comprises determining coordinates of the vessel center in the vicinity of the cursor.

4. A method as defined in claim 1 wherein the step of determining values of one or more parameters comprises determining directions of the vessel walls in the vicinity of the cursor.

5. A method as defined in claim 1 further comprising the steps of determining from the wall coordinates a wall center of gravity of pixels defining an upper vessel wall and a wall center of gravity of pixels defining a lower vessel wall, and determining vessel diameter and vessel center coordinates from the centers of gravities of the pixels defining the upper and lower vessel walls.

6. A method as defined in claim 1 further comprising the step of repeating steps a) and b) at predefined intervals.

7. A method as defined in claim 1 wherein the step of determining values of one or more parameters comprises determining vessel center coordinates, wherein the step of automatically moving the cursor comprises the steps of moving the cursor to the vessel center coordinates in the ultrasound image, rotating the cursor into alignment with a vessel direction, moving the cursor along the vessel in the vessel direction to a new position and repeating steps a) and b) at the new position.

8. A method as defined in claim 7 wherein the step of moving the cursor to a new position comprises sensing contact between the cursor and the vessel wall in the ultrasound image.

9. A method as defined in claim 8 wherein the step of sensing contact between the cursor and the vessel wall comprises moving the cursor by incremental moves and comparing a pixel value of the image with a threshold value representative of the vessel wall after each incremental move.

10. A method as defined in claim 8 further comprising repeating steps a) and b) when contact between the cursor and the vessel wall is sensed.

11. A method as defined in claim 7 wherein the step of moving the cursor to a new position comprises moving the cursor by a distance approximately equal to the vessel diameter in the vicinity of the cursor.

12. A method as defined in claim 7 wherein the step of moving the cursor to a new position comprises sensing an end of the vessel in said ultrasound image.

13. A method as defined in claim 12, wherein the step of sensing the end of the vessel in said ultrasound image comprises determining that the upper and lower vessel wall directions exceed a predetermined angle.

14. A method as defined in claim 7 further comprising the step of identifying coordinates of a smallest diameter of the vessel and highlighting the smallest diameter of the vessel in said ultrasound image.

15. Apparatus for measurement and analysis of patient anatomy comprising:

an ultrasound imaging system for generating an ultrasound image of a region of a patient and for providing coordinates of walls of a vessel in the image;

means responsive to placement of a cursor within the vessel in the ultrasound image for determining from the wall coordinates values of one or more parameters of the vessel in the vicinity of the cursor;

means for recording the determined parameter values; and means for automatically moving the cursor to a plurality of positions along the vessel, determining values of said one or more parameters at each of said plurality of positions and recording the determined parameter values, thereby automatically tracking the vessel.

16. Apparatus as defined in claim 15, wherein said means for determining values of one or more parameters comprises means for determining a diameter of the vessel in the vicinity of the cursor.

17. Apparatus as defined in claim 15, wherein said means for determining values of one or more parameters of the vessel comprises means for determining coordinates of the vessel center in the vicinity of the cursor.

18. Apparatus as defined in claim 15, wherein said means for determining values of one or more parameters comprises means for determining directions of the vessel walls in the vicinity of the cursor.

19. Apparatus as defined in claim 15, further comprising means for determining from the wall coordinates a center of gravity of pixels defining an upper vessel wall and a center of gravity of pixels defining a lower vessel wall and means for determining vessel diameter and vessel center coordinates from the centers of gravities of the pixels defining the upper and lower vessel walls.

20. Apparatus as defined in claim 15, wherein said means for determining values of one or more parameters comprises means for determining vessel center coordinates and wherein said means for automatically moving the cursor comprises means for moving the cursor to the vessel center coordinates in the ultrasound image, means for rotating the cursor into alignment with a vessel direction and means for moving the cursor along the vessel in the vessel direction to a new position.

21. Apparatus as defined in claim 20, wherein said means for moving the cursor comprises means for sensing contact of the cursor with the vessel wall in the ultrasound image.

22. Apparatus as defined in claim 21, wherein said means for sensing contact comprises means for moving the cursor by incremental moves and means for comparing a pixel value of the image with a threshold value representative of the vessel wall after each incremental move.

23. Apparatus as defined in claim 15, further comprising means for identifying coordinates of a smallest diameter of the vessel and highlighting the smallest diameter in ultrasound image.

24. A method for measurement and analysis of patient anatomy with an ultrasound imaging system which generates an ultrasound image of a region of a patient and provides coordinates of walls of a vessel in the image, said ultrasound imaging system executing the steps of:

a) in response to placement of a cursor within the vessel in the ultrasound image, automatically determining vessel center coordinates in the vicinity of the cursor;

b) automatically moving the cursor to the vessel center coordinates in the ultrasound image;

c) automatically rotating the cursor into alignment with the vessel;

d) automatically moving the cursor along the vessel in the cursor direction to a new position;

e) automatically determining vessel center coordinates at the new position; and f) automatically repeating steps b) to e) to provide automatic tracking of the vessel center.

\* \* \* \* \*